(12) United States Patent
Moawia et al.

(10) Patent No.: US 8,329,915 B2
(45) Date of Patent: Dec. 11, 2012

(54) THIENOTHIOPHENE DERIVATIVES

(75) Inventors: Omer E. Ahmed Moawia, Singapore (SG); Ashok Mishra, Singapore (SG); Andrew Grimsdale, Singapore (SG); Siu Choon Ng, Singapore (SG); Subodh G. Mhaisalkar, Singapore (SG); Beng Ong, Singapore (SG); Zhikuan Chen, Singapore (SG)

(73) Assignees: Nanyang Technological University, Singapore (SG); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 12/918,717

(22) PCT Filed: Feb. 19, 2009

(86) PCT No.: PCT/SG2009/000058
§ 371 (c)(1),
(2), (4) Date: Aug. 20, 2010

(87) PCT Pub. No.: WO2009/105042
PCT Pub. Date: Aug. 27, 2009

(65) Prior Publication Data
US 2010/0331550 A1  Dec. 30, 2010

Related U.S. Application Data

(60) Provisional application No. 61/030,770, filed on Feb. 22, 2008.

(51) Int. Cl.
*C07D 495/04* (2006.01)
*C07D 285/10* (2006.01)

(52) U.S. Cl. .......................................... 548/126; 549/50
(58) Field of Classification Search .................. 548/126; 549/50
See application file for complete search history.

(56) References Cited

FOREIGN PATENT DOCUMENTS
JP     2007-088224 A      4/2007
JP     2007088224 A   *  4/2007

OTHER PUBLICATIONS

Medina et al. Chemistry of Materials (2007), 19(20), p. 4949-4956.*
H. Kong et al., "New Amorphous Semiconducting Copolymers Containing Fluorene and Thiopene Moieties for Organic Thin-Film Transistors", *J. Mater. Chem.*, Mar. 10, 2008, vol. 18 pp. 1895-1902.

* cited by examiner

*Primary Examiner* — Yong Chu
(74) *Attorney, Agent, or Firm* — Dickstein Shapiro LLP

(57) ABSTRACT

An organic compound represented by the following general formula (I) and characterized by the conjugation of thieno[3,2-b]thiophene, thiophene and phenylene units in the conjugated compound.

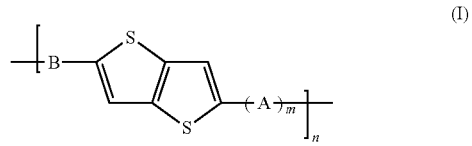

13 Claims, 7 Drawing Sheets

THIENOTHIOPHENE DERIVATIVES

This application is a 371 of International Application No. PCT/SG2009/000058, filed on Feb. 20, 2009, which claims the benefit of U.S. Provisional Application No. 61/030,770, filed on Feb. 22, 2008.

BACKGROUND OF THE INVENTION

The present invention relates generally to organic compounds for semiconductor applications.

Organic materials have recently received enormous interest over their silicon analogues because they can potentially be used to fabricate organic thin-film transistors (OTFTs) at low cost, over large coverage areas, and on flexible substrates. However, many known organic semiconductors suffer a number of drawbacks such as, for example, susceptibility to air oxidation and/or limited solubility even in hot solvents. Further, use of expensive processing techniques such as vacuum deposition is required for solid materials, making such materials unsuitable for fabricating of large-area films. Accordingly, it would be desirable to have an air-stable and more soluble organic semiconductor material in order to fully realise the potential benefits of organic electronics.

SUMMARY OF THE INVENTION

The invention provides compounds that are particularly useful when employed as semiconductors in electronic devices such as organic field effect transistors (OFETs), organic solar-cell devices and organic light-emitting diodes (OLEDs).

In a first aspect, the invention provides a compound of formula (I):

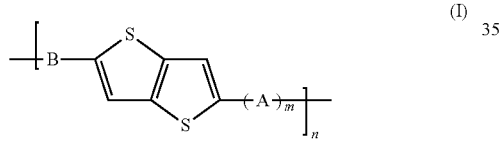

(I)

wherein
n is an integer from 1 to 1000, inclusive;
  wherein when n is 1,
    m is 1;
    A is a moiety of formula (i):

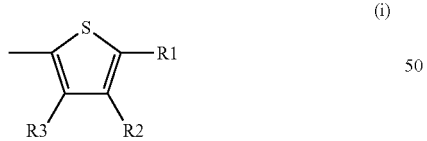

(i)

wherein
      R1 is aryl or heteroaryl, and
      R2 and R3 are independently H or alkyl; and
    B is a moiety of formula (ii):

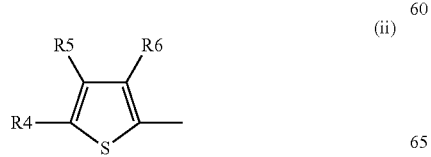

(ii)

wherein
  R4 is aryl or heteroaryl, and
  R5 and R6 are independently H or alkyl; and
wherein when n is greater than 1,
  m is 0 or 1;
  A is a moiety of formula (iii) or (iv):

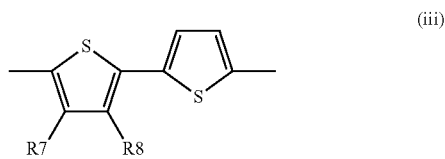

(iii)

wherein R7 and R8 are independently H or alkyl;

(iv)

wherein R9 is H or alkyl; and
B is a moiety of formula (v), (vi) or (vii):

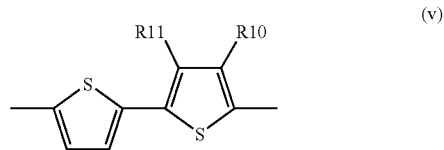

(v)

wherein R10 and R11 are independently H or alkyl;

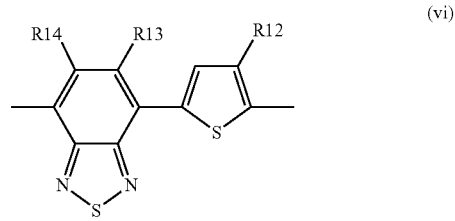

(vi)

wherein R12, R13 and R14 are independently H or alkyl;

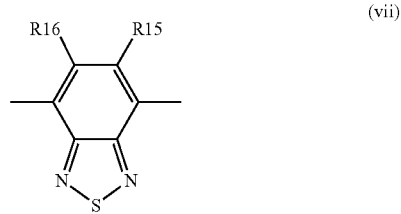

(vii)

wherein R15 and R16 are independently H or alkyl.

In some examples, R1 and R4 may independently be phenyl, naphthalenyl, thiophenyl or dodecylphenyl.

In some examples, R2, R3, R5 and R6 may independently be H or dodecyl.

In some examples, R7 to R16 may independently be H, dodecyl, tetradecyl, or cetyl.

In some examples, n may be an integer from 1 to 100, inclusive.

In another aspect, the invention provides an organic semiconductor material comprising a compound of formula (I) as defined above.

In another aspect, the invention provides an organic semiconductor device comprising a layer of an organic semiconductor material, the organic semiconductor material comprising a compound of formula (I) as defined above.

Other objects, features, advantages and aspects of the present invention will become apparent to those skilled in the art from the following description and appended claims. It should be understood, however, that the following description, appended claims, and specific examples, while indicating preferred embodiments of the invention, are given by way of illustration only. Various changes and modifications within the spirit and scope of the disclosed invention will become readily apparent to those skilled in the art from reading the following.

DETAILED DESCRIPTION

Figure 1:
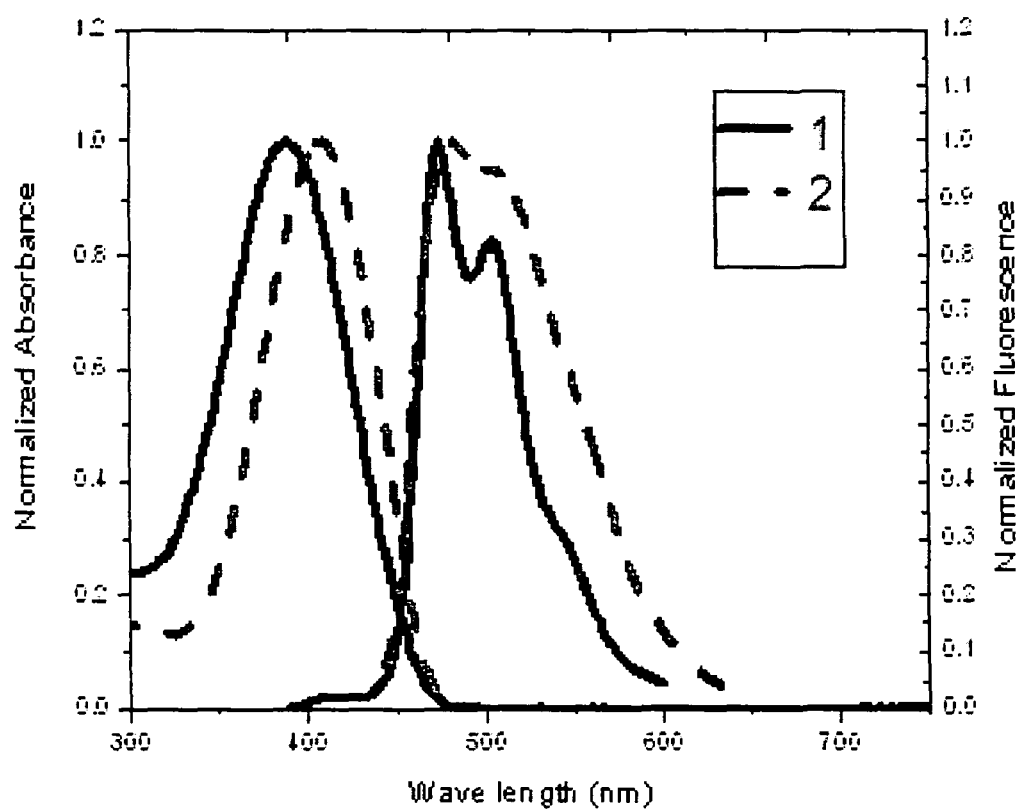
FIGS. 1 and 2 are graphs illustrating the UV-vis and fluorescence spectra of exemplary compounds of the present invention.

Listed below are definitions of various terms used to describe the compounds of the present invention. These definitions apply to the terms as they are used throughout the specification unless they are otherwise limited in specific instances either individually or as part of a larger group.

The term "alkyl" as used herein refers to branched or straight chain hydrocarbon groups, comprising preferably 1 to 20 carbon atoms. Examples of alkyl groups include, but are not limited to, methyl, ethyl, propyl, butyl, heptyl, nonyl, decyl, undecyl, dodecyl, tetradecyl, cetyl, 2-ethylhexyl, 3,7-dimethyloctyl, etc. An alkyl group may be unsubstituted or optionally substituted with one or more substituents selected from halogen, lower alkyl, and the like. Examples of substituted alkyl groups include, but are not limited to, haloalkyl groups such as, for example, 1-bromododecane, 6-bromohexyl, and the like or other substituted alkyl groups such as, for example, 6-methoxyhexyl, 8-methoxyoctyl, alkylthio (e.g., ω-thiomethyl, hexylthio and octylthio), and the like.

The term "lower alkyl" as used herein refers to branched or straight chain alkyl groups comprising 1 to 6 carbon atoms, preferably 1 to 4 carbon atoms. Examples of lower alkyl groups include, but are not limited to, methyl, ethyl, n-propyl, i-propyl, n-butyl, i-butyl, sec-butyl, t-butyl, pentyl, and hexyl. A lower alkyl group may be unsubstituted or optionally substituted with one or more substituents including, but not limited to, substituents such as halogen, and the like.

The term "aryl" as used herein refers to an aromatic ring having 6 to 18 carbon atoms and includes monocyclic groups as well as multicyclic groups, e.g. fused groups such as bicyclic and tricyclic groups. Preferred aryl groups are those which contain from 6 to 12 carbon atoms, preferably 6 carbon atoms for monocyclic rings and 9 or 10 carbon atoms for fused bicyclic rings. Examples include, but are not limited to, phenyl group, naphthyl group and anthracenyl group, especially phenyl group. An aryl group may be unsubstituted or substituted at one or more ring positions with one or more substituents selected from, for example, halogen, alkyl group, and the like.

The term "heteroaryl" means an aromatic ring having 5 to 18 atoms, preferably 5 or 6 atoms, including at least one heteroatom, such as, but not limited to, N, O and S, within the ring. The term "heteroaryl" includes monocyclic groups as well as multicyclic groups, e.g. fused groups such as bicyclic and tricyclic groups. The heteroaryl may optionally be fused or bridged with one or more benzene rings and/or to a further heteroaryl ring and/or to an alicyclic ring.

The term "halo" or "halogen" as used herein refers to F, Cl, Br or I.

The term "substituted" is intended to describe moieties having substituents replacing a hydrogen atom on one or more atoms, e.g. C, O or N, of a molecule.

As described herein above, the present invention relates to compounds of formula (I) and to use of such compounds in semiconductor applications.

Preferred are compounds of formula (I) wherein R1 and R4 are independently phenyl, naphthalenyl, thiophenyl or dodecylphenyl. Advantageously, aryl units such as phenyl and naphthalene when used as 'end-cap' substituents provide stability against oxidation.

Also preferred are compounds of formula (I) wherein R2, R3, R5 and R6 are independently H or dodecyl. Advantageously, introduction of two alkyl chains at the 3 or 4-position on thiophene increases solubility and thus facilitates device fabrication. The presence of long alkyl chains in the compounds of formula (I) also improves their molecular ordering, thus positively influencing their semiconducting properties.

Also preferred are compounds of formula (I) wherein R7 to R16 are independently H, dodecyl, tetradecyl, or cetyl.

Some examples of the compounds of formula (I) are shown by the following structural formulas, but the present invention is not limited to these embodiments.

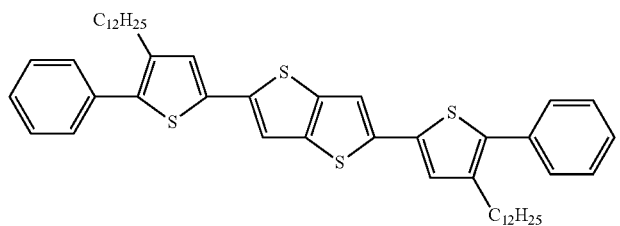 1
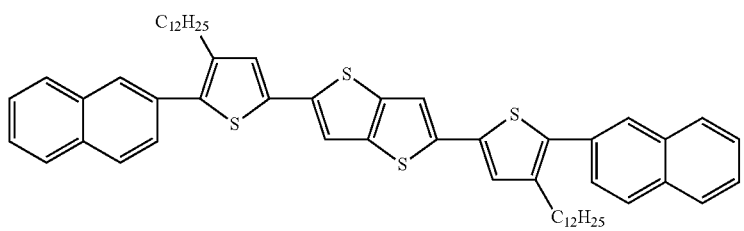 2
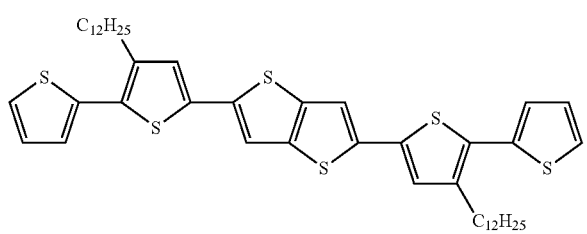 3
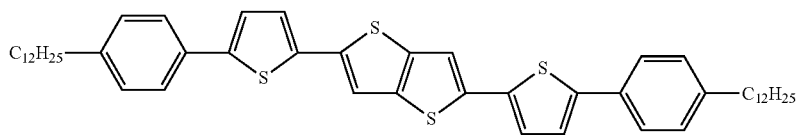 4
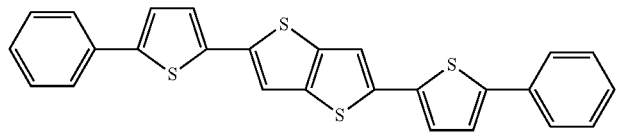 5
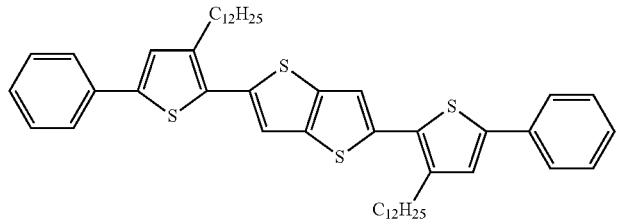 6
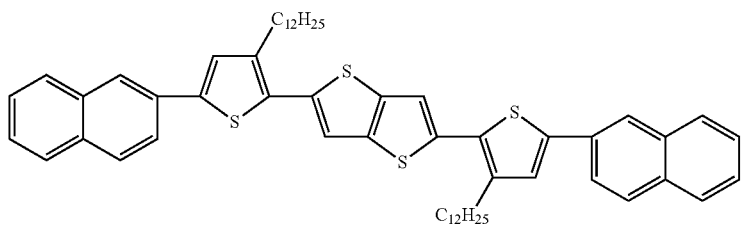 7

-continued
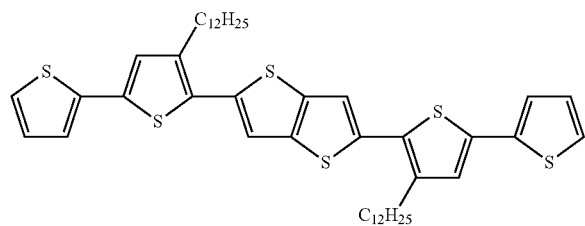
8
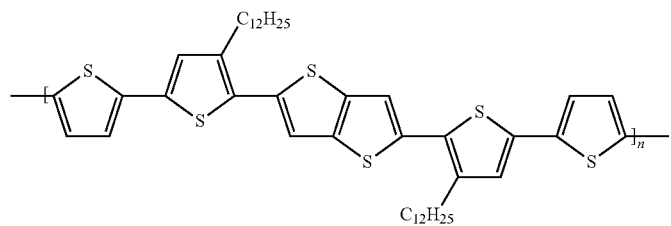
9
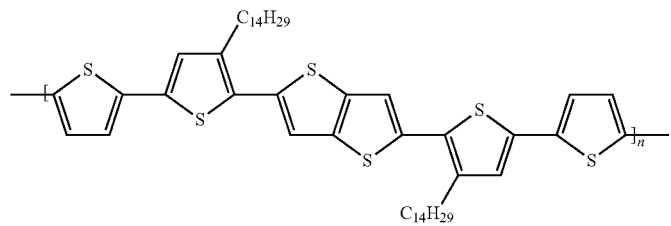
10
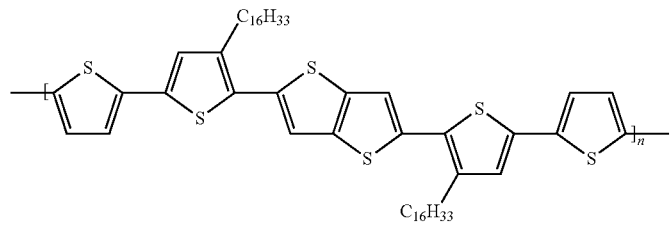
11
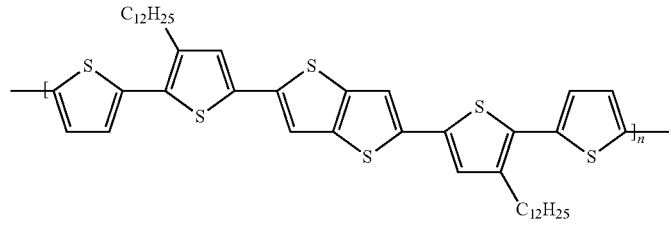
12
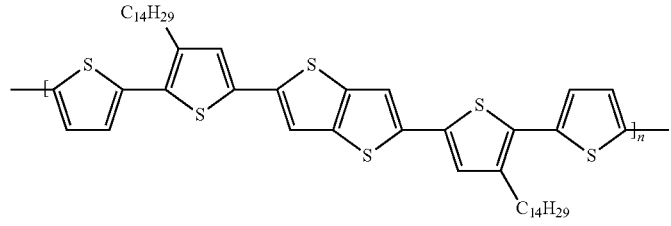
13
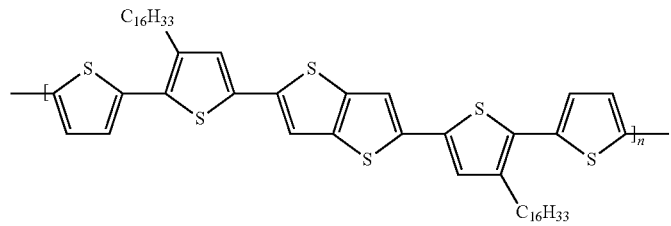
14

-continued
15
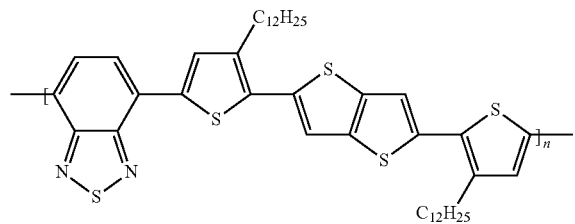
16
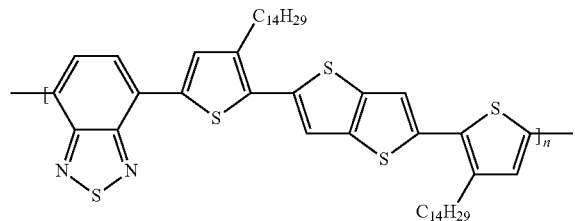
17
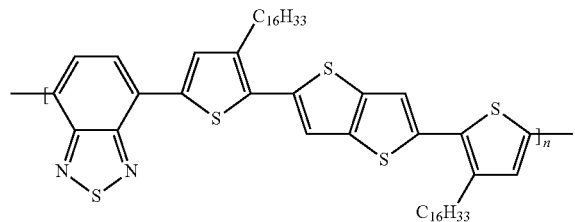
18
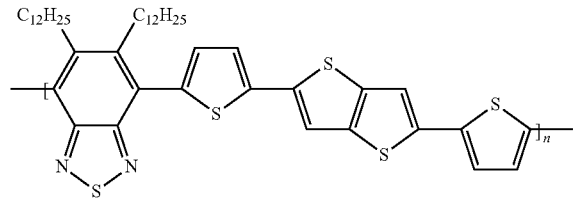
19
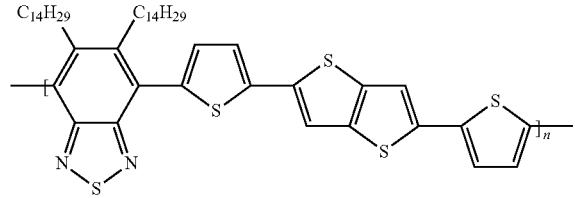
20
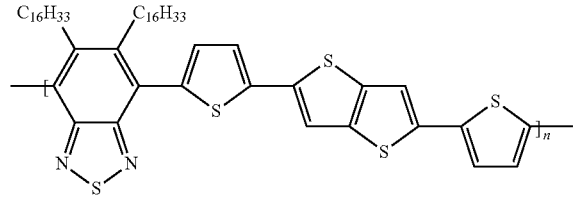
21
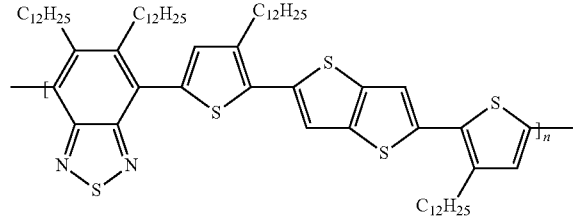

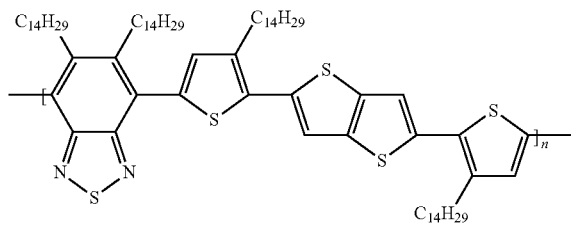

22

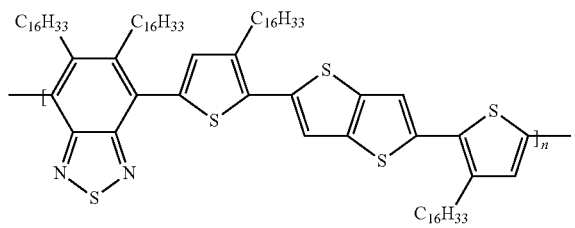

23

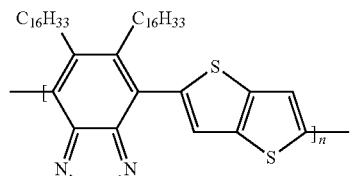

24

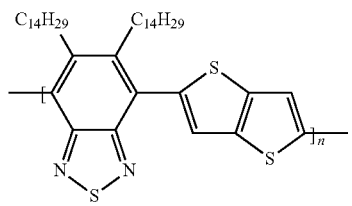

25

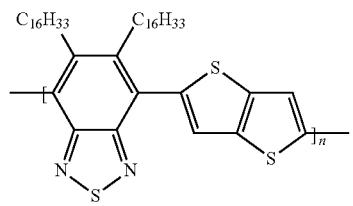

26

Compounds provided by the invention are hereinafter designated as "compound(s) of the invention".

It will be appreciated that the compounds of the invention may exist in the form of optical isomers, racemates or diastereoisomers. The scope of this invention embraces all stereochemically isomeric forms of the compounds.

The term "stereochemically isomeric forms" as used herein therefore means all possible isomeric forms which the compounds of the invention may possess. Unless otherwise mentioned or indicated, the chemical structures, systematic names and formulae of the compounds denote the mixture of all possible stereochemically isomeric forms, containing all diastereomers and enantiomers of the basic molecular structure. In particular, stereogenic centers may have the R- or S-configuration.

Compounds of the present invention are particularly useful when employed as semiconductors in electronic devices such as organic field effect transistors (OFETs), organic solar-cell devices and organic light-emitting diodes (OLEDs).

Organic semiconductor materials of the present invention are easily synthesized, have good air and thermal stability, are easily processable and may be readily deposited by spin-coating methods from solution in organic solvents.

The compounds of the present invention achieve excellent thin film transistor (TFT) performances with good mobilities. Organic thin film transistor (OTFT) devices based on compounds of the present invention have high stability in air when exposed to ambient lighting and ambient environment and exhibit excellent field-effect performances, with a mobility as high as $3.11 \times 10^{-2}$ cm$^2$/V·s for a top-contact OTFT made by spin-coating in ambient air and $1.4 \times 10^{-4}$ cm$^2$/V·s for a bottom-contact OTFT deposited by thermal evaporation. The HOMO energy levels of all the materials are in the range of 5.2-5.27 eV, which match well with work function of the gold electrodes, favoring the charge injection of holes. Thermal analyses as well as electrochemical measurement data confirm that the compounds of the present invention afford good thermal and oxidation stability.

General Synthetic Methods

The compounds of the present invention may be prepared by the methods depicted in the reaction schemes shown below. The starting materials and reagents used in preparing these compounds are either available commercially or are prepared by methods known to those skilled in the art. These schemes are merely illustrative of some of the methods by which the compounds of this invention can be synthesized, and various modifications to these schemes can be made and will be suggested to one skilled in the art having referred to this disclosure.

SCHEME A: Synthesis of Compounds 1 to 5

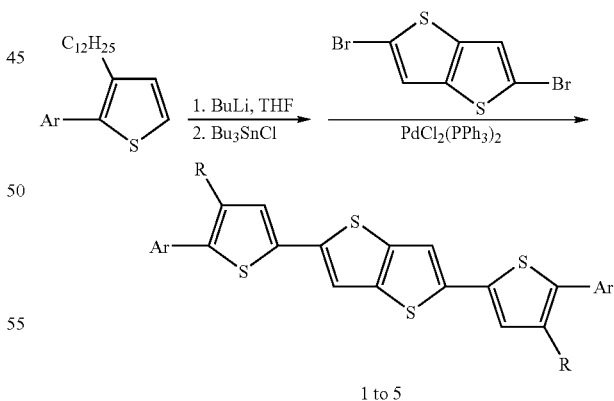

1 to 5

Compounds 1 to 5 are synthesized by stille coupling using a one-pot method between 2,5-dibromothieno[3,2-b]thiophene and two equivalents of the corresponding freshly prepared tri-n-butylstannyl derivatives of [tributyl(4-dodecyl-5-phenyl-thiophen-2-yl)stannane (1), tributyl(4-dodecyl-5-naphthalen-2-yl-thiophen-2-yl)stannane (2) and tributyl (thiophen-2-yl)stannane (3)], in the presence of catalytic (1 Mol %) PdCl$_2$(PPh$_3$)$_2$ in refluxing dry THF in 87% yield.

All the compounds are very soluble in organic solvents, such as, CHCl$_3$, toluene, THF, etc., and are easily purified by column chromatography and recrystallization. Both compounds 4 and 5 have lower solubility in common organic solvents than compounds 1 to 3, making them unsuitable candidates for liquid phase device fabrication. The structures of compounds 1 to 3 were characterized by $^1$H, $^{13}$C NMR, elemental analysis and MALDI-TOFF mass spectrometry. The results were consistent with their predicted chemical structures. However, characterization of both compounds 4 and 5, by solution phase techniques was not possible due to their low solubility in organic solvents. Therefore, their structures were only confirmed by MALDI-TOFF mass spectrometry.

SCHEME B: Synthesis of Compounds 6 to 8

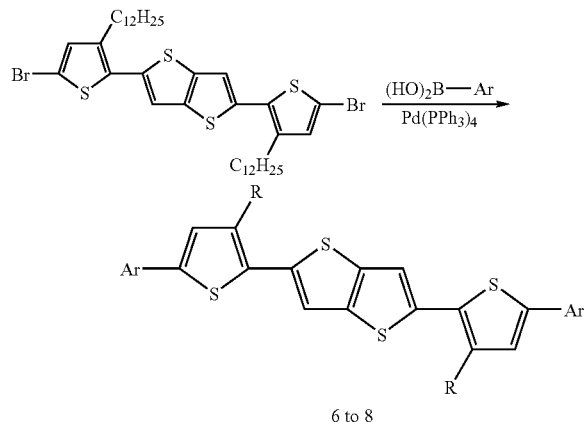

6 to 8

Compounds 6 to 8 are synthesized by a Suzuki coupling reaction between 2,5-bis(5-bromo-3-dodecylthiophen-2-yl) thieno[3,2-b]thiophene and two equivalents of the appropriate aryl-boronic acid [phenylboronic acid (6), naphthalen-2-ylboronic acid (7) and thiophen-2-ylboronic acid (8)] with Pd(PPh3)$_4$ in refluxing THF in 70% yield.

All the compounds are very soluble in organic solvents, such as, CHCl$_3$, toluene, THF, etc., and can be easily purified by column chromatography and recrystallization. The structures of compounds 6 to 8 were characterized by $^1$H, $^{13}$C NMR, elemental analysis and MALDI-TOFF mass spectrometry. The results were consistent with their predicted chemical structures.

SCHEME C: Synthesis of Compounds 9 to 14

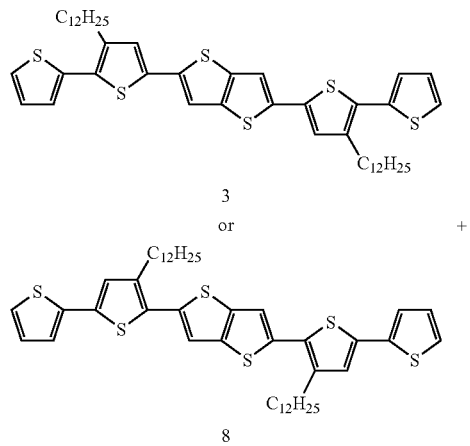

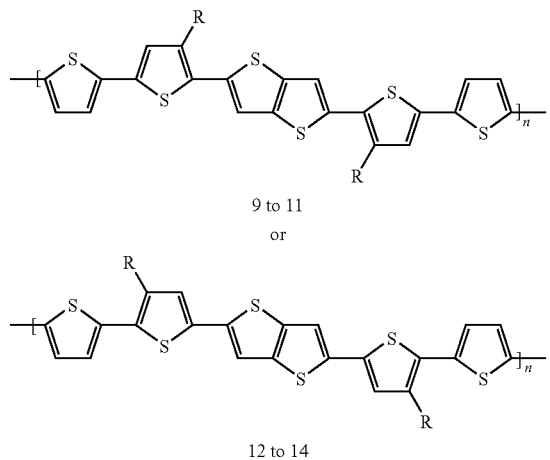

9 to 11 or 12 to 14

Compounds 9 to 14 are synthesized by direct chemical oxidative polymerization of compounds 3 and 8 respectively with four equivalents of ferric chloride as the oxidant in chloroform.

SCHEME D: Synthesis of Compounds 15 to 26

Compounds 15 to 26 are synthesized by stille coupling or Suzuki coupling.

EXAMPLES

The invention is described with reference to the following examples. It is to be appreciated that the invention is not limited to these examples.

Example 1

Properties of Compounds 1, 2, 6 and 7

The thermal properties of these compounds were determined by differential scanning calorimetry (DSC) and thermogravimetric analysis (TGA) under nitrogen and the results are summarized in Table 1 below. All the materials melted above 100° C. and have relatively high thermal stability (>350° C.).

Figure 2:
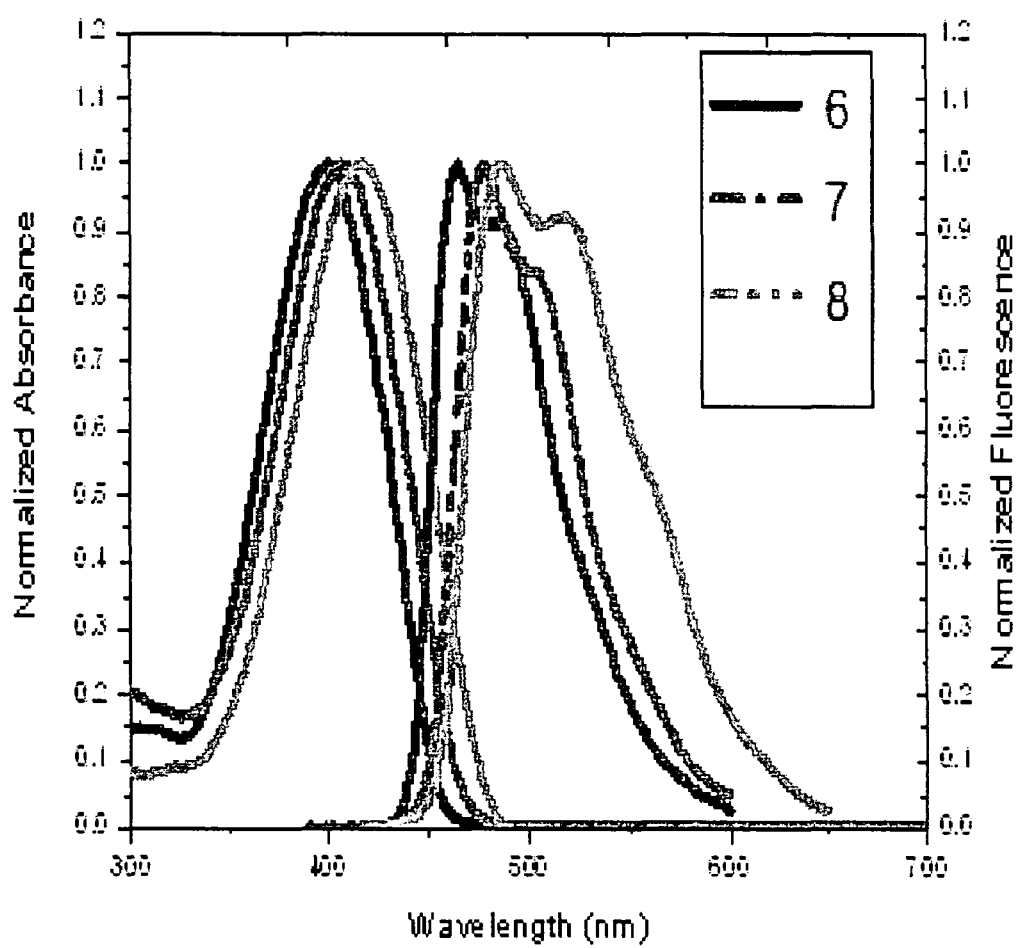

The photophysical properties of the compounds were measured by UV-vis and fluorescence spectroscopy in THF and the results are presented in Table 1 below. All the compounds show strong absorption and emission in the 350-420 and 470-480 nm ranges respectively (see FIGS. 1 and 2).

Figure 3:
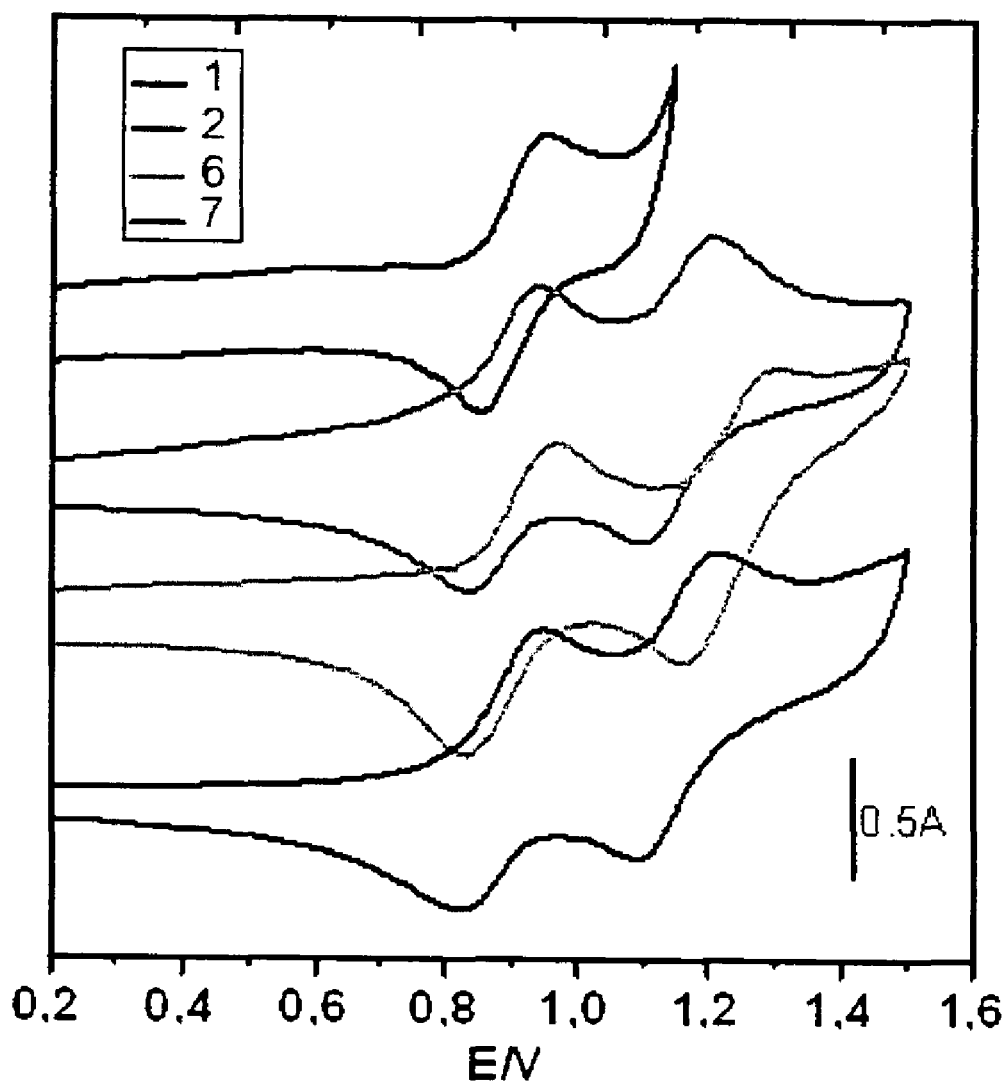
FIG. 3 is a graph illustrating cyclic voltammetry (CV) measurements obtained from exemplary compounds of the present invention.

The oxidation potentials of compounds 1, 2, 6 and 7 measured by cyclic voltammetry (CV) are 0.87, 0.80, 0.84 and 0.81 V, respectively, from which the HOMO levels were calculated as shown in Table 1 and FIG. 3. As their reduction potentials could not be observed, the LUMO levels were estimated from the HOMO-LUMO energy gaps which were estimated from the end-absorptions of the UV-Vis spectra are −2.56 (−2.61, −2.51 and −2.54 eV) for compounds 1, 2, 6 and 7, respectively. The HOMO levels of all the compounds match well with the work function of metallic gold (−5.1 eV) and can therefore enhance hole charge injection between the electrode and the semiconductor, thereby greatly improving device performance.

TABLE 1

| | $T_m$ (°C.)[a] | $T_d$ (°C.)[b] | UV-vis $\lambda_{max}$ (nm)[c] | PL $\lambda_{max}$ (nm)[c] | HOMO/LUMO (band gap) (eV)[f] |
|---|---|---|---|---|---|
| 1 | 124 | 360 | 389 | 474 | −5.25/−2.54 (2.71) |
| 2 | 114 | 395 | 409 | 480 | −5.20/−2.61 (2.66) |
| 6 | 117 | 397 | 401 | 465 | −5.28/−2.55 (2.73) |
| 7 | 118 | 400 | 407 | 478 | −5.21/−2.54 (2.67) |

[a] Obtained from DSC measurement
[b] Obtained from TGA measurement
[c] Measured in a THF solution
[f] Calculated from CV and UV-Vis absorption spectra band edge

Example 2

OFET Device Performance

Figure 4:
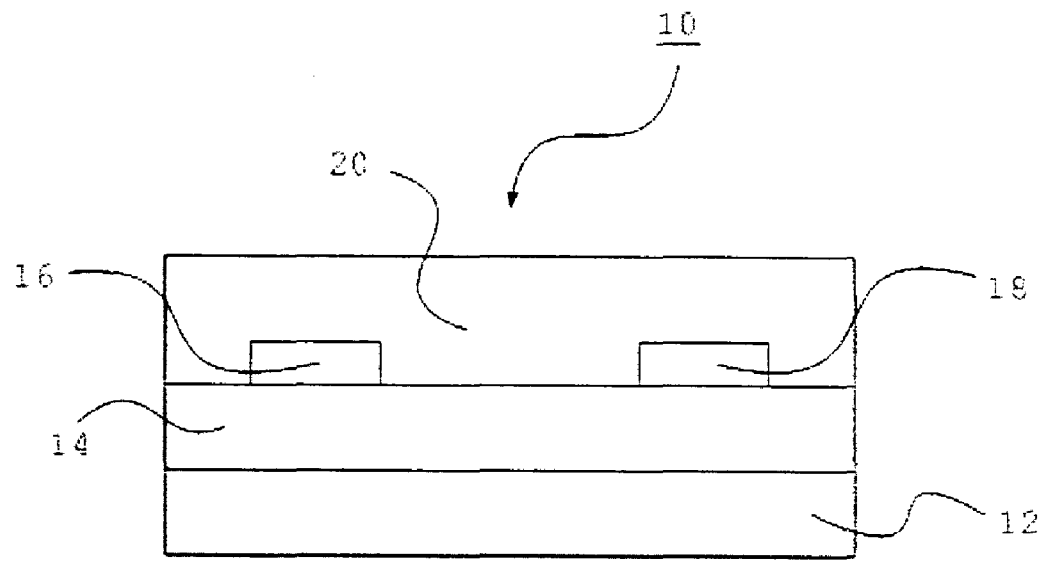
FIG. 4 is an enlarged cross-sectional view of an organic field effect transistor (OFET) in accordance with an embodiment of the present invention.
Figure 5:
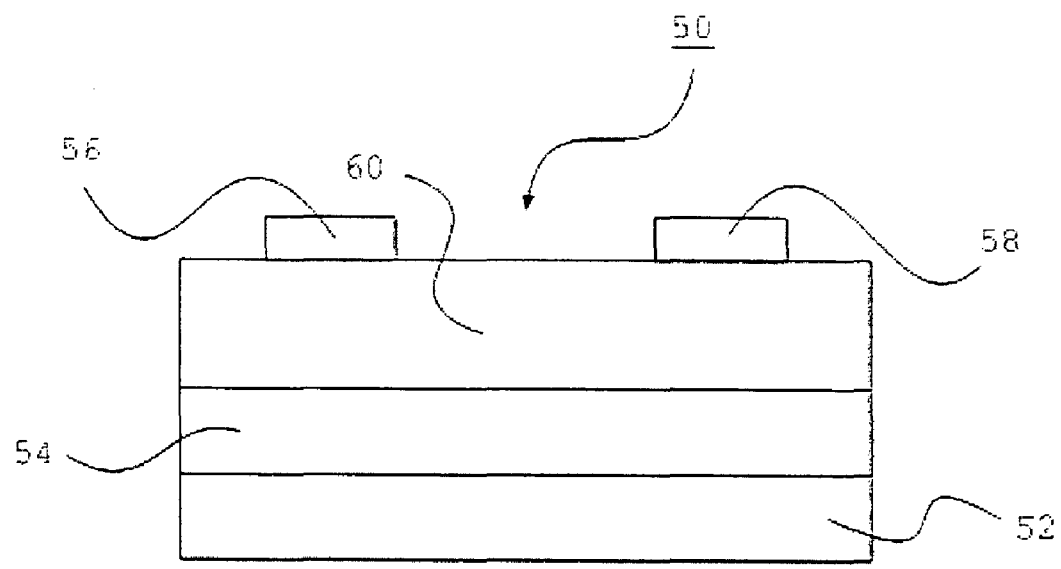
FIG. 5 is an enlarged cross-sectional view of an OFET in accordance with another embodiment of the present invention.

For the purpose of confirming the device characteristics of the organic semiconductor material according to an embodiment of the present invention, field-effect transistors were made both in bottom-contact (semiconductor deposited above the drain and source electrodes) and top-contact (drain and source deposited above the semiconductor) device geometries by both solution deposition and vacuum thermal evaporation. Referring now to FIGS. 4 and 5, enlarged cross-sectional views of the field-effect transistors 10 and 50 are shown. A heavily doped Si wafer was used as substrate and gate electrode 12 and 52 with 100 nm thermally grown $SiO_2$ serving as gate dielectric 14 and 54. Before thin film deposition, the Si wafer was cleaned by piranha ($H_2O_2:H_2SO_4$, in the ratio of 1:2) followed by SC1 ($NH_4OH:H_2O_2:H_2O$, in the ratio of 1:1:10).

For the bottom-contact structure 10, the gold layer (source 16 and drain 18) with a thickness of 100 nm was sputter-deposited and patterned by photolithography and lift-off to define the source and drain electrodes 16 and 18.

For the top-contact structure 50, the gold electrodes (source 56 and drain 58) were thermally evaporated and defined using a shadow mask with a film thickness of 40 nm.

Respective layers 20 and 60 of an organic semiconductor material of the present invention are formed on the gate dielectric 14 and 54 as a channel layer.

All the transistors were characterized under $N_2$ environment. From the electrical transfer characteristics ($I_d$-$V_g$), the parameters such as carrier mobility, threshold voltage, current on/off ratio, and subthreshold swing were obtained. The carrier mobility was calculated from the saturation regime at a drain-source voltage of −30 V and a gate-source voltage of −30 V. In order to minimize the leakage current, every device was isolated by scratching a trench around the active device area with a probe tip to remove the organic semiconductor from the trench:

a. Solution-Processed OFET

All solution processed devices using bottom contact geometry, in general, showed lower charge carrier mobility than those using the top contact geometry. The bottom-contact devices have a channel length of 11120 μm and a channel width of 30 μm.

A smooth and continuous film was obtained by spin coating using toluene solutions. Various concentrations ranging from 0.05 wt. % to 0.5 wt. % were used. A uniform film with good connectivity was obtained from toluene solution with a concentration of 0.5 wt. %. Annealing temperatures of from 100° C. to 180° C., annealing times of from 15 minutes to 40 minutes and annealing atmospheres under both vacuum and $N_2$ were also studied. It was found that higher annealing temperatures ($T_{anneal}$>120° C.) resulted in poorer device performance and there is no obvious enhancement in device performance with longer annealing times. Vacuum oven annealing and cooling down overnight resulted in better performance.

Figure 6:
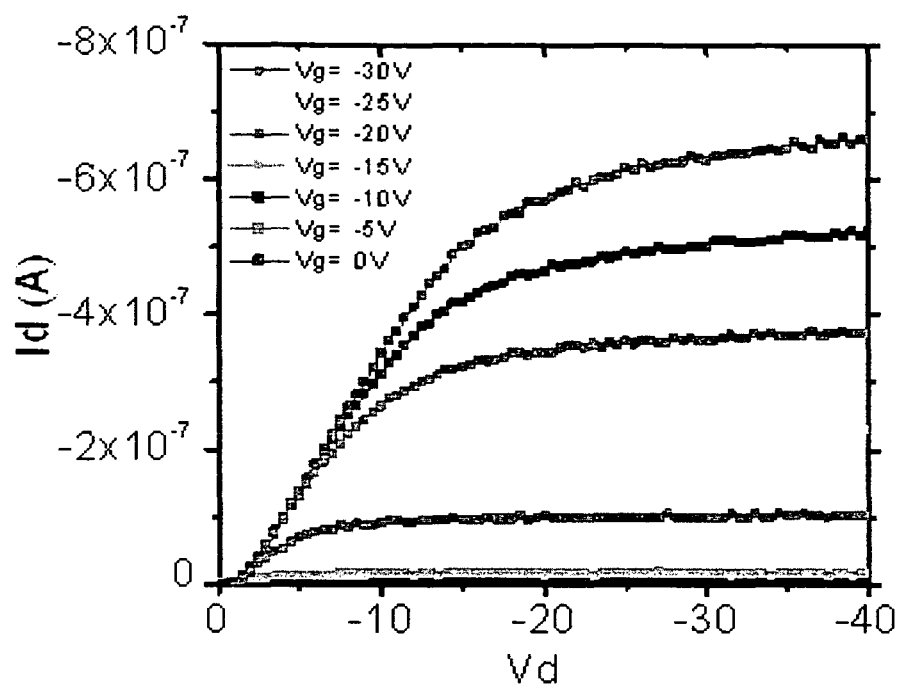
FIGS. 6 and 7 are graphs illustrating the output and transfer characteristics of a bottom contact device made from an exemplary solution processed compound of the present invention.
Figure 7:
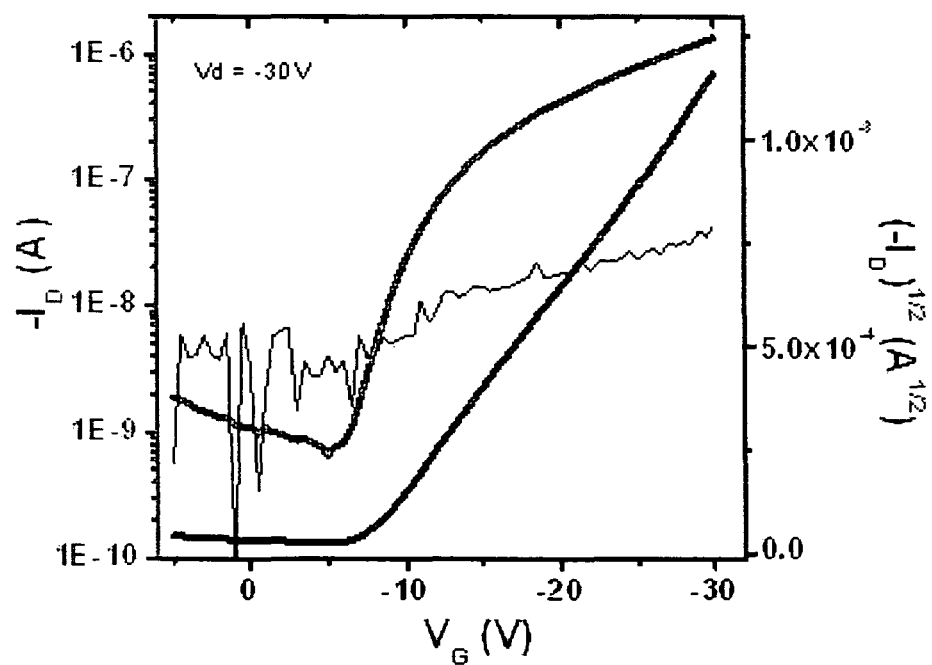
Figure 8:
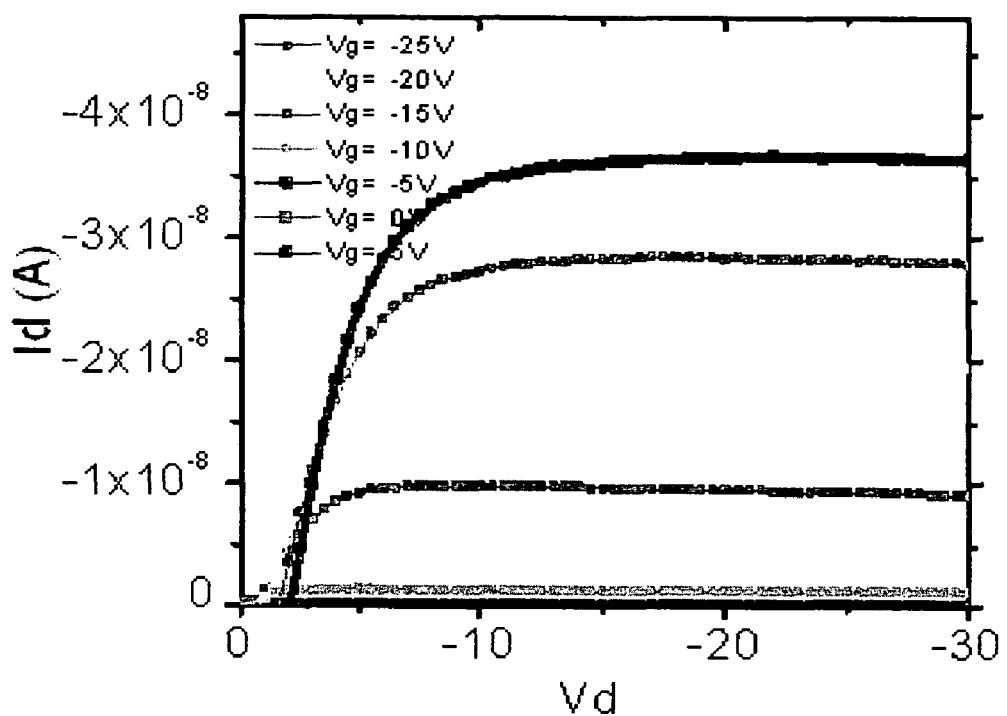
FIGS. 8 and 9 are graphs illustrating the output and transfer characteristics of a top contact device made from an exemplary solution processed compound of the present invention.
Figure 9:
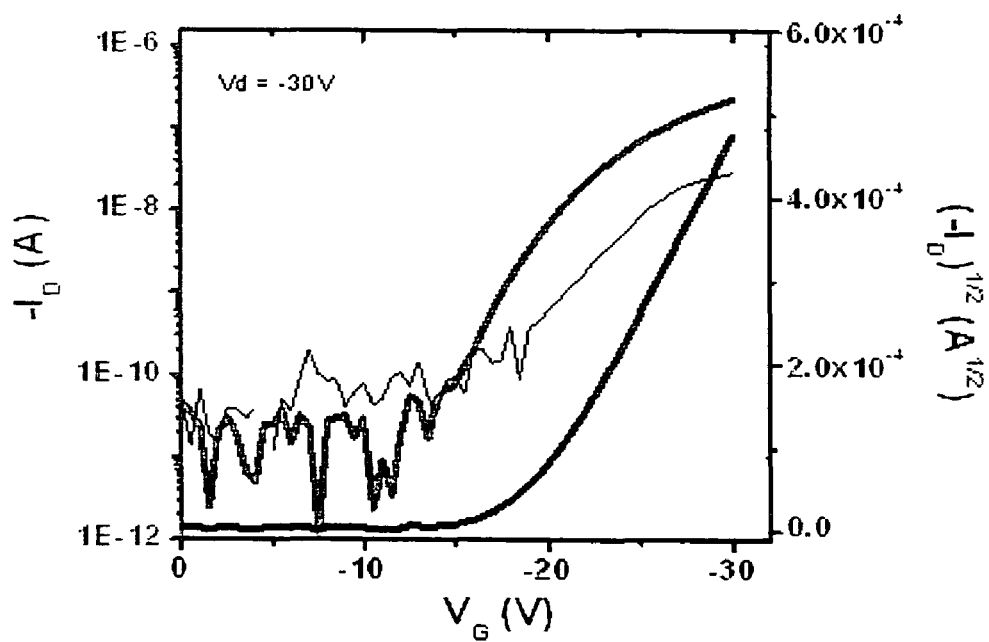

FET electrical characteristics of a bottom-contact TFT made from compound 1 spin-coated in ambient air are shown in FIGS. 6 and 7, while the FET electrical characteristics of a top-contact TFT made from compound 1 spin-coated in ambient air are shown in FIGS. 8 and 9.

Compound 1 was spin coated at a rate of 1000 rpm for 100 seconds from 0.5 wt. % solution in toluene. Annealing took place in a vacuum oven at a temperature of 70° C. for 1 hour, followed by 100° C. for 20 minutes. It was then cooled under vacuum overnight to ensure molecular ordering.

The bottom-contact device was shown to have a carrier mobility of $5.11 \times 10^{-4}$ $cm^2/V \cdot s$, a subthreshold slope of 0.98 V/decade, and an on/off ratio of $2 \times 10^3$. Comparatively, the top-contact device outperformed the bottom-contact TFTs with a higher carrier mobility of $3.11 \times 10^{-2}$ $cm^2/V \cdot s$, a lower subthreshold slope of 0.4 V/decade, and a higher on/off ratio of $4.5 \times 10^4$.

b. Thermal-Evaporation Deposited OFET

Compound 1 was also deposited by thermal evaporation in a vacuum (<$1 \times 10^{-6}$ Torr) at a stable deposition rate of near 1 nm/min. Substrates were intentionally heated at 100° C. during the deposition. After deposition, the films were kept under high vacuum and annealed at 100° C. for another 20 minutes. The resultant film was very smooth and had good connectivity.

Figure 10:
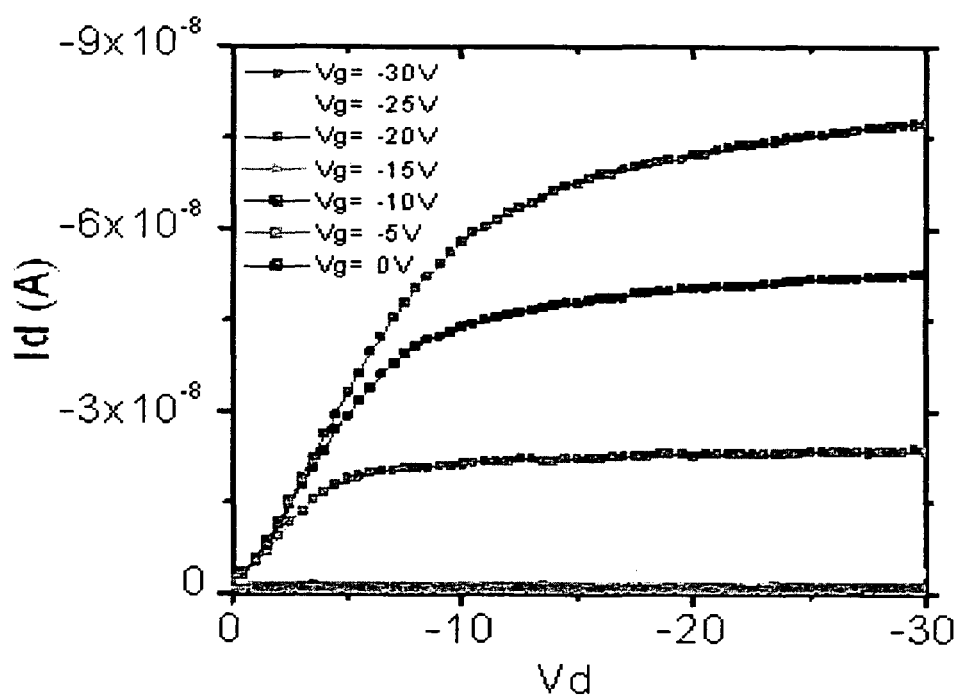
FIGS. 10 and 11 are graphs illustrating the output and transfer characteristics of a bottom contact device made from an exemplary compound of the present invention deposited by thermal evaporation.
Figure 11:
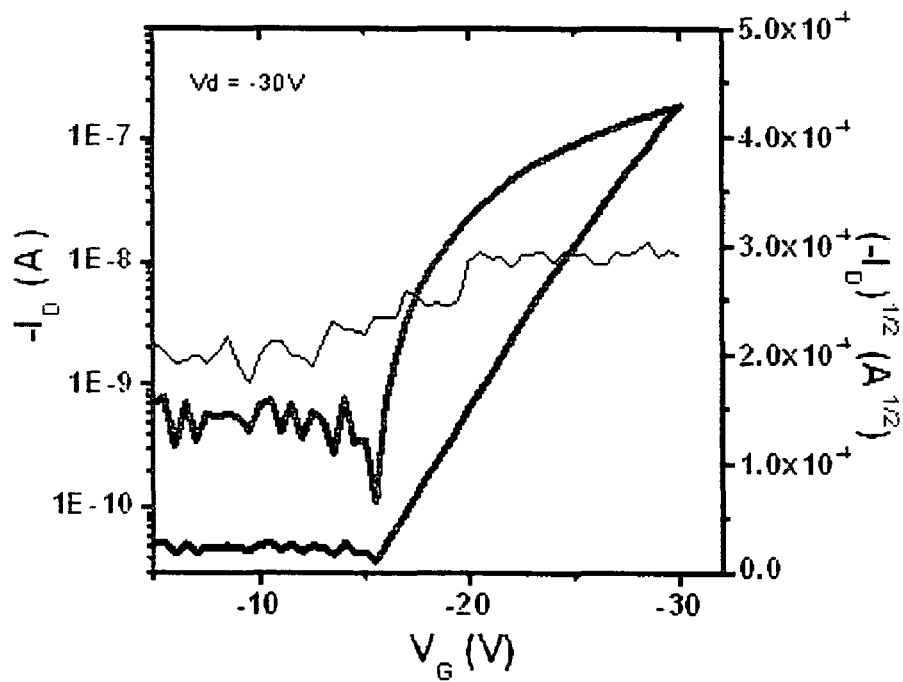

FIGS. 10 and 11 show the electrical characteristics of a bottom-contact OTFT made from compound 1 deposited by thermal evaporation. The device shows a mobility of $1.4 \times 10^{-4}$ $cm^2/V \cdot s$, a subthreshold slope of 1.1 V/decade and an on/off ratio of $2.5 \times 10^3$. Accordingly, it is concluded that the performance of the thermally evaporated bottom-contact device keeps at the same level as the solution spin-coated one.

The description of the preferred embodiments of the present invention has been presented for purposes of illustration and description, but is not intended to be exhaustive or to limit the invention to the forms disclosed. It will be appreciated by those skilled in the art that changes could be made to the embodiments described above without departing from the broad inventive concept thereof. It is understood, therefore, that this invention is not limited to the particular embodiments disclosed, but covers modifications within the spirit and scope of the present invention as defined by the appended claims.

ABBREVIATIONS

BuLi=n-butyllithium
$Bu_3SnCl$=tri-n-butyltin chloride
$(HO)_2B$—Ar=aryl-boronic acid
HOMO=Highest Occupied Molecular Orbital
LUMO=Lowest Unoccupied Molecular Orbital
$PdCl_2(PPh_3)_2$=dichlorobis(triphenylphosphine)palladium (II)
$Pd(PPh_3)_4$=tetrakis(triphenylphosphine)palladium
PL $\lambda_{max}$=Wavelength of maximum photoluminescence emission
RT=room temperature
$T_d$=decomposition temperature
THF=tetrahydrofuran
$T_m$=melting temperature
UV-vis UV-vis $\lambda_{max}$=Wavelength of maximum absorption in UV-Vis spectrum

The invention claimed is:
1. A compound of formula (I):

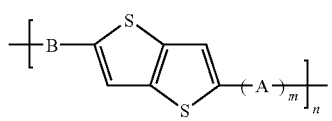

wherein
n is an integer from 2 to 1000, inclusive;
m is 1;
A is a moiety of formula (iii) or (iv):

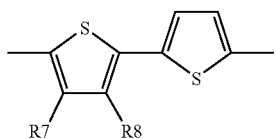

wherein R7 and R8 are independently H or alkyl;

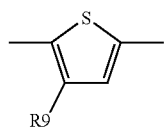

wherein R9 is H or alkyl; and
B is a moiety of formula (v), (vi) or (vii):

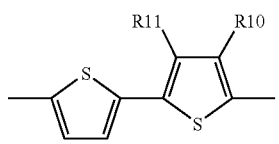

wherein R10 and R11 are independently H or alkyl;

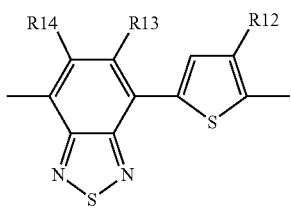

wherein R12, R13 and R14 are independently H or alkyl;

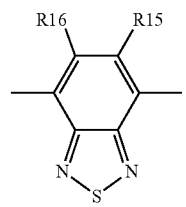

wherein R15 and R16 are independently H or alkyl.
2. The compound of claim 1, wherein R7 to R16 are independently H, dodecyl, tetradecyl, or cetyl.

3. The compound of claim 1, wherein the compound is represented by the following general formula (I-1):

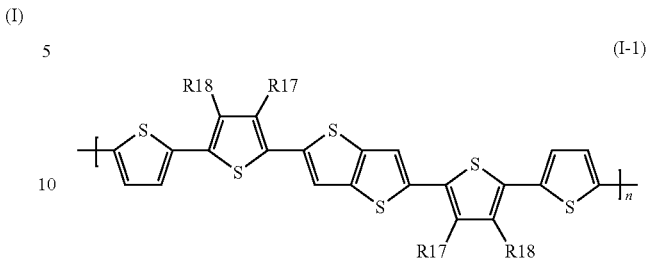

wherein R17 and R18 are independently H, dodecyl, tetradecyl, or cetyl.
4. The compound of claim 3, wherein R17 is H and R18 is dodecyl, tetradecyl, or cetyl.
5. The compound of claim 3, wherein R18 is H and R17 is dodecyl, tetradecyl, or cetyl.
6. The compound of claim 1, wherein the compound is represented by the following general formula (I-2):

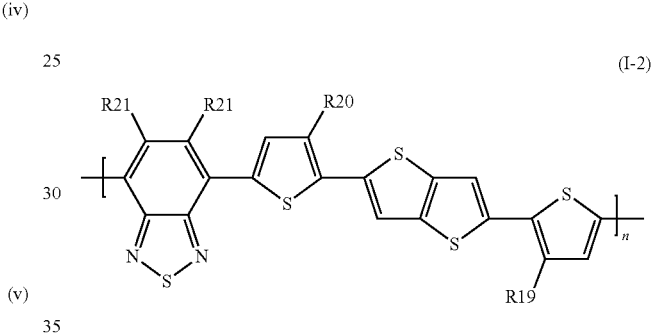

wherein R19, R20 and R21 are independently H, dodecyl, tetradecyl, or cetyl.
7. The compound of claim 6, wherein R21 is H, and R19 and R20 are independently dodecyl, tetradecyl, or cetyl.
8. The compound of claim 6, wherein R19 and R20 are H, and R21 is dodecyl, tetradecyl, or cetyl.
9. The compound of claim 6, wherein R19, R20 and R21 are independently dodecyl, tetradecyl, or cetyl.
10. The compound of claim 1, wherein the compound is represented by the following general formula (I-3):

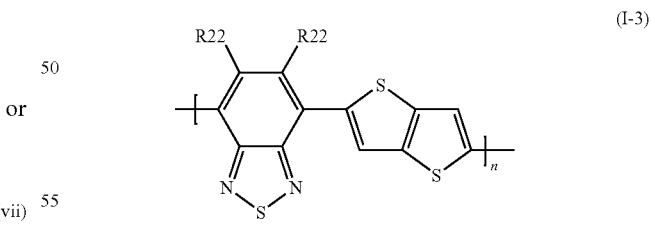

wherein R22 is dodecyl, tetradecyl, or cetyl.
11. The compound of claim 1, wherein n is an integer from 2 to 100, inclusive.
12. An organic semiconductor material comprising a compound of claim 1.
13. An organic semiconductor device comprising a layer of an organic semiconductor material of claim 12.

* * * * *